United States Patent [19]
Shepard

[11] Patent Number: 5,595,485
[45] Date of Patent: Jan. 21, 1997

[54] DENTAL RECORDING DEVICE, ARTICULATOR AND METHODS

[75] Inventor: John S. Shepard, Fort Collins, Colo.

[73] Assignee: John S. Shepard, D.D.S., P.C., Fort Collins, Colo.

[21] Appl. No.: 342,598

[22] Filed: Nov. 21, 1994

[51] Int. Cl.[6] .................................................. A61C 11/00
[52] U.S. Cl. ........................................ 433/58; 433/55
[58] Field of Search ........................ 433/54, 55, 56, 433/57, 58, 59, 60, 61, 62, 63, 65, 68, 71

[56] References Cited

U.S. PATENT DOCUMENTS

| | | | |
|---|---|---|---|
| 1,989,367 | 1/1935 | Keeney | 433/58 |
| 2,608,761 | 9/1952 | Scott | 433/56 |
| 3,409,986 | 11/1968 | Freeman | 433/55 |
| 4,047,302 | 9/1977 | Cheythey | 433/56 |
| 4,279,595 | 7/1981 | Della Croce | 433/55 |
| 4,504,226 | 3/1985 | Gordon | 433/63 |
| 4,900,254 | 2/1990 | Gama | 433/65 |
| 5,020,993 | 6/1991 | Levandoski | 433/65 |

Primary Examiner—Robert P. Swiatek
Assistant Examiner—Yvonne R. Abbott
Attorney, Agent, or Firm—Ancel W. Lewis, Jr.

[57] ABSTRACT

A jaw movement recording device, articulator and methods disclosed utilize a lower marking plate with front, rear, left and right side marking pins that cooperate with an upper marking plate and depressions and a bearing pin in such a way as to give an accurate recording of the movement of a patient's lower jaw in a wafer between the two plates. An articulator has a lower frame with upright side posts having upper pin-like portions and an upper frame with fossa holders and a pliable material that form fossa socket patterns. Tension springs extending between the frames at the front and rear enable a constant tension in forming the fossa socket patterns.

7 Claims, 5 Drawing Sheets

DENTAL RECORDING DEVICE, ARTICULATOR AND METHODS

TECHNICAL FIELD

This invention relates to a dental apparatus and method for recording jaw movements, for duplicating the jaw movement of a patient for use in making dentures and duplicating the position of real teeth and the like.

BACKGROUND ART

A common dental problem is that many dentures are so constructed that when the patient bites down there are high spots or openings between the teeth and many times the dentures are displaced producing denture sores on the gum due to pressure points produced and an uneven bite. A variety of recording devices and articulators have heretofore been provided for this purpose.

Reith U.S. Pat. No. 2,043,394 discloses an articulator with depending pins in an upper frame forming recordings in cups in upstanding side posts supported by a lower frame. A pair of coil springs along the sides hold tension on the upper frame as it is moved relative to a lower frame.

Highkin U.S. Pat. No. 2,754,589 discloses a method of and apparatus for making dentures using an articulator having three marking pins disposed in a triangular arrangement.

The Della Croce U.S. Pat. Nos. 4,273,533, 4,276,022 and 4,279,595 disclose an articulator having an upper marking plate with three depending marking pins in a triangular arrangement. A pair of side posts of the articulator are attached to and depend from the upper frame.

Lee U.S. Pat. No. 4,556,387 discloses an articulator having T-shaped upper and lower frames and vertical side posts with an adjustably mounted incisal pin at the front that rests on a pad. A pair of upstanding side pins supported by the side posts fit in down facing socket surfaces on the upper frame.

Wilcox U.S. Pat. No. 4,981,437 discloses a method and apparatus for making dentures showing tracing plates for an articulator having four projections in an upper tracing plate extending toward the lower jaw and arranged in a trapezoidal arrangement with two on each side of a vertical center line and each bearing pin in a lower tracing plate. The upper tracing plate extends across the top of and does not fit within the upper edentulous ridge.

DISCLOSURE OF THE INVENTION

A jaw movement recording device, articulator and methods disclosed duplicate the patient's temporomandibular joint in such a way as to avoid uneven bites and undue displacement of dentures produced using the recording device and methods on an articulator. The recording device includes a lower marking plate sized and shaped to fit within the lower edentulous ridge. The lower marking plate has four upstanding marking pins arranged in a diamond-shaped configuration. An upper marking plate fits within the upper edentulous ridge and has four depressions that receive upper end portions of the marking pins and also has a central bearing pin projecting downwardly. A wafer is formed between the lower and upper plates and the lower jaw of a patient is moved so that four socket patterns are formed in the wafer that are a representation of the movement of the patient's lower jaw. An articulator has an upper frame carrying a pair of laterally spaced side fossa holders containing what is initially a pliable mold material and receive upstanding top pin portions on side posts attached to a lower frame. Tension means along both sides and at the front hold the upper and lower frames together so that four mandibular joint socket patterns are formed in the mold material in side fossa holders the socket patterns representing the mandibular joint socket of each patient. The articulator supports a patient's dentures and the upper frame is movable relative to the lower frame with the top pin portions moving in the socket patterns to simulate each patient's jaw movement.

BRIEF DESCRIPTION OF THE DRAWINGS

Details of this invention are described in connection with the accompanying drawings which like parts bear similar reference numerals in which.

DETAILED DESCRIPTION

The preliminary procedure followed to obtain information on the mouth of a particular patient will first be described. A primary impression of the patient's upper and lower edentulous ridges is made with an alginate impression material. These upper and lower alginate primary impressions in the upper and lower trays are filled with dental stone to make a set of upper and lower study models called upper and lower primary study models. A silicone separating or spacing material is placed over these primary study models. Upper and lower acrylic secondary impressions are made in trays for both upper and lower edentulous ridges. Dental stone secondary study models are poured up from the secondary impressions. Upper and lower base plates are made on these secondary study models. Each of these upper and lower base plates will have a cured medical silicone lining so that they fit the patient's mouth exactly.

The above described upper and lower base plates are placed in the patient's mouth to make neutral zones. The lower base plate is made first. A heavy white silicone material is injected on the surface of the lower base plate and is placed in the patient's mouth. The patient forms the neutral zone by swallowing thus forming by the cheeks on one side and the tongue on the other side the silicone into a rim that represents where the teeth would be if they had not been lost. The lower base plate is then trimmed flat on top to the approximate height of the missing teeth. This is repeated for forming the upper base plate.

Figure 1:
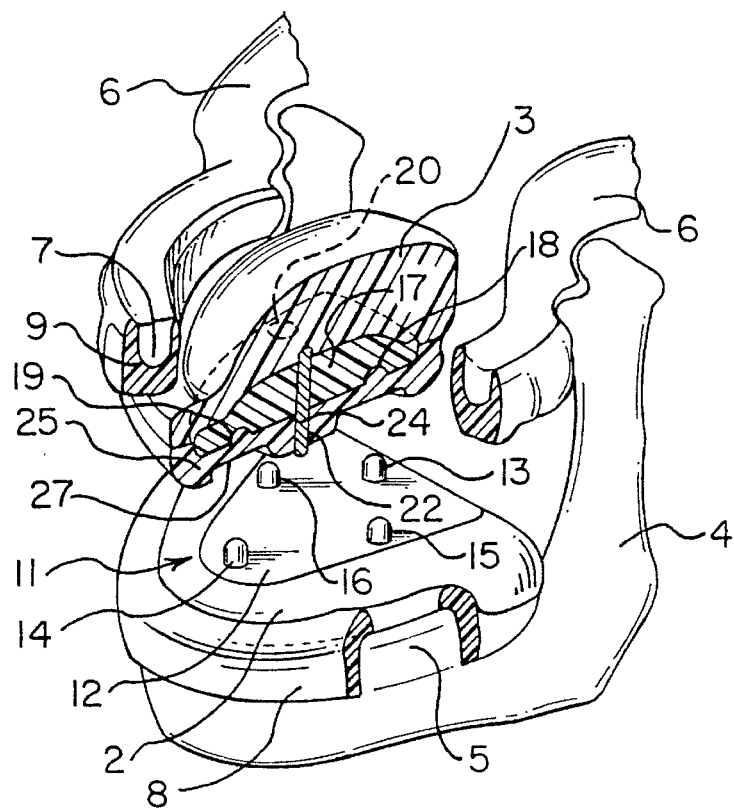
FIG. 1 is a top perspective view with portions broken away to show portions of the upper and lower jaws of a patient and a jaw movement recording device mounted on upper and lower base plates in the patient's mouth.
Figure 2:
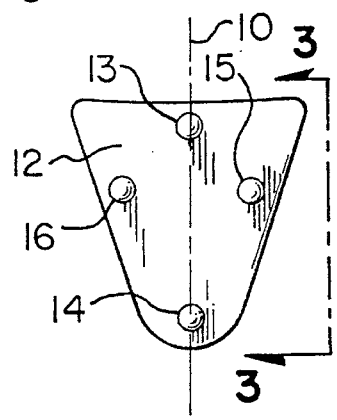
FIG. 2 is a top plan view of the lower marking plate shown in FIG. 1.
Figure 3:
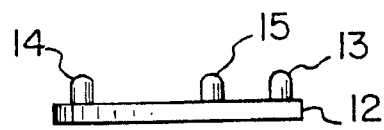
FIG. 3 is a side elevation view of the lower marking plate taken along line 3—3 of FIG. 2.
Figure 5:
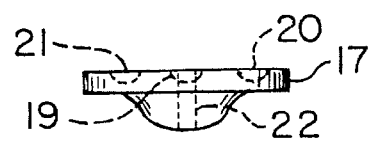
FIG. 5 is an end elevation view of the upper marking plate taken along line 5—5 of FIG. 4.
Figure 6:
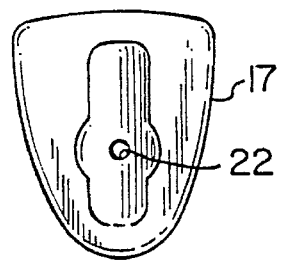
FIG. 6 is a plan view of the upper marking plate as viewed on the opposite face from that shown in FIG. 4.
Figure 4:
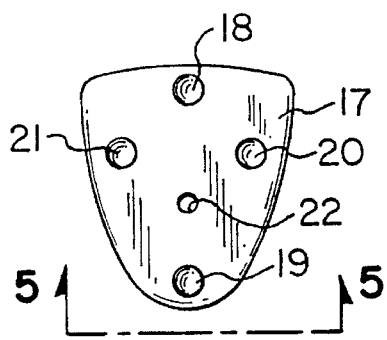
FIG. 4 is a plan view of the upper marking plate looking from below upwardly toward the upper jaw.

Referring now to FIG. 1 there is shown portions of the lower jaw 4 and lower edentulous ridge 5 and the upper jaw 6 and upper edentulous ridge 7 of a patient. A lower base plate 8 constructed as above described is shown mounted over the lower edentulous ridge 5 and an upper base plate 9 also constructed as above described is shown mounted over the upper edentulous ridge 7.

In FIG. 1 there is shown in the patient's mouth a jaw movement recording device generally designated by numeral 11 which includes a lower marking plate 12 and an upper marking plate 17. The lower marking plate 12 has a rear marking pin 13, a front marking pin 14 along a longitudinal center line 10 a selected distance from one another, left side marking pin 15 and right side marking pin 16 spaced from one another a selected distance in a diamond-shaped array. The configuration of the marking pins is generally diamond-shaped and more specifically the rear marking pin is in a triangular-shaped configuration with the left and right side marking pins and the front marking pin in a triangular-shaped configuration with the left and right side marking pins with the front marking pin being a greater distance from a line through the left and right side pins than the rear marking pin. The location designations are with respect to the patient's jaw. That is the front pin is at the front of the jaw and the left pin on the left side of the jaw. The lower marking plate is generally triangular being wider at the rear and narrower at the front. The lower marking plate 12 is sized and shaped to fit within and be substantially confined within the lower edentulous ridge 5 of the lower jaw of the patient. The four marking pins extend upwardly toward the roof of the patient's mouth, have rounded top surfaces and are arranged to give a three-dimensional jaw movement without lifting off.

In the procedure for mounting the lower and upper base plates and upper and lower marking devices in the mouth, the lower marking plate 12 is attached to the lower base plate 8 and this is done using a soft plastic lower body 2. This plastic is initially soft and moldable and hardens when exposed to the air for a short length of time. Body 2 is known in the trade as friendly plastic. The plates 12 and 8 and body 2 are chilled in cold water to set the plastic body 2 which serves to fasten plate 12 to base plate 8. Next the upper base plate 9 has a soft plastic upper body 3 placed in the palate area.

Figure 7:
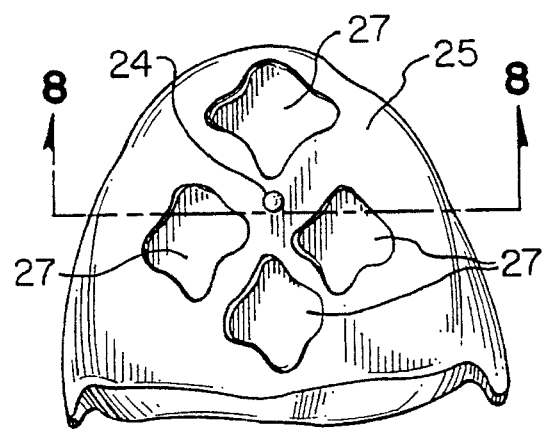
FIG. 7 is a plan view of the wafer with four socket patterns.
Figure 8:
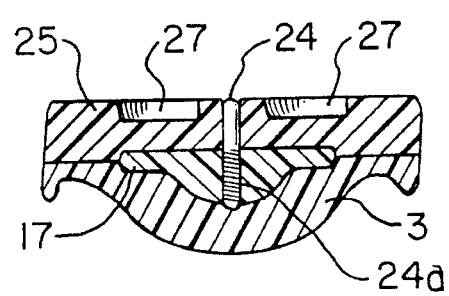
FIG. 8 is a sectional view taken along line 8—8 of FIG. 7.
Figure 11:
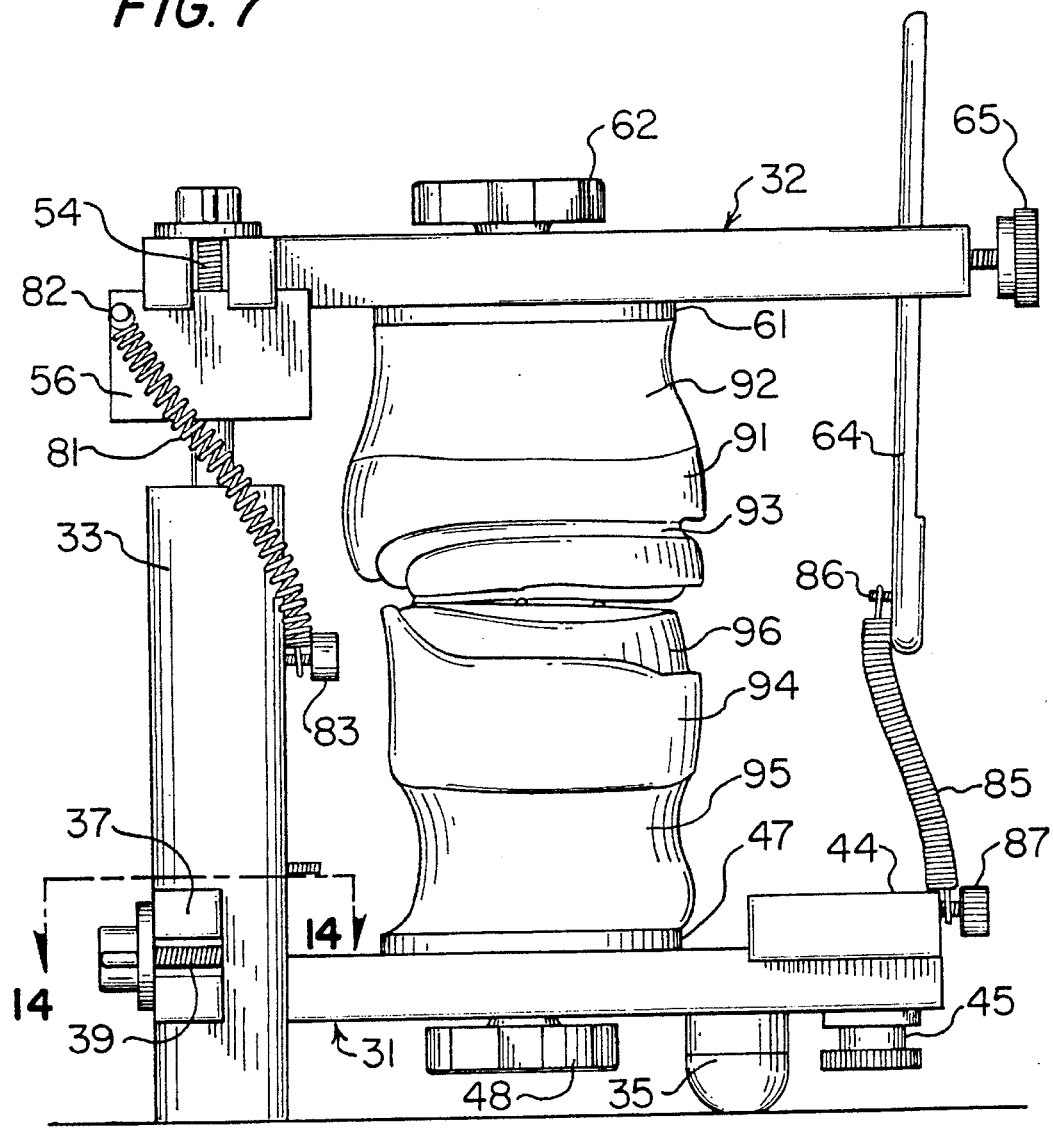
FIG. 11 is a side elevational view of an articulator embodying features of the present invention.
Figure 12:
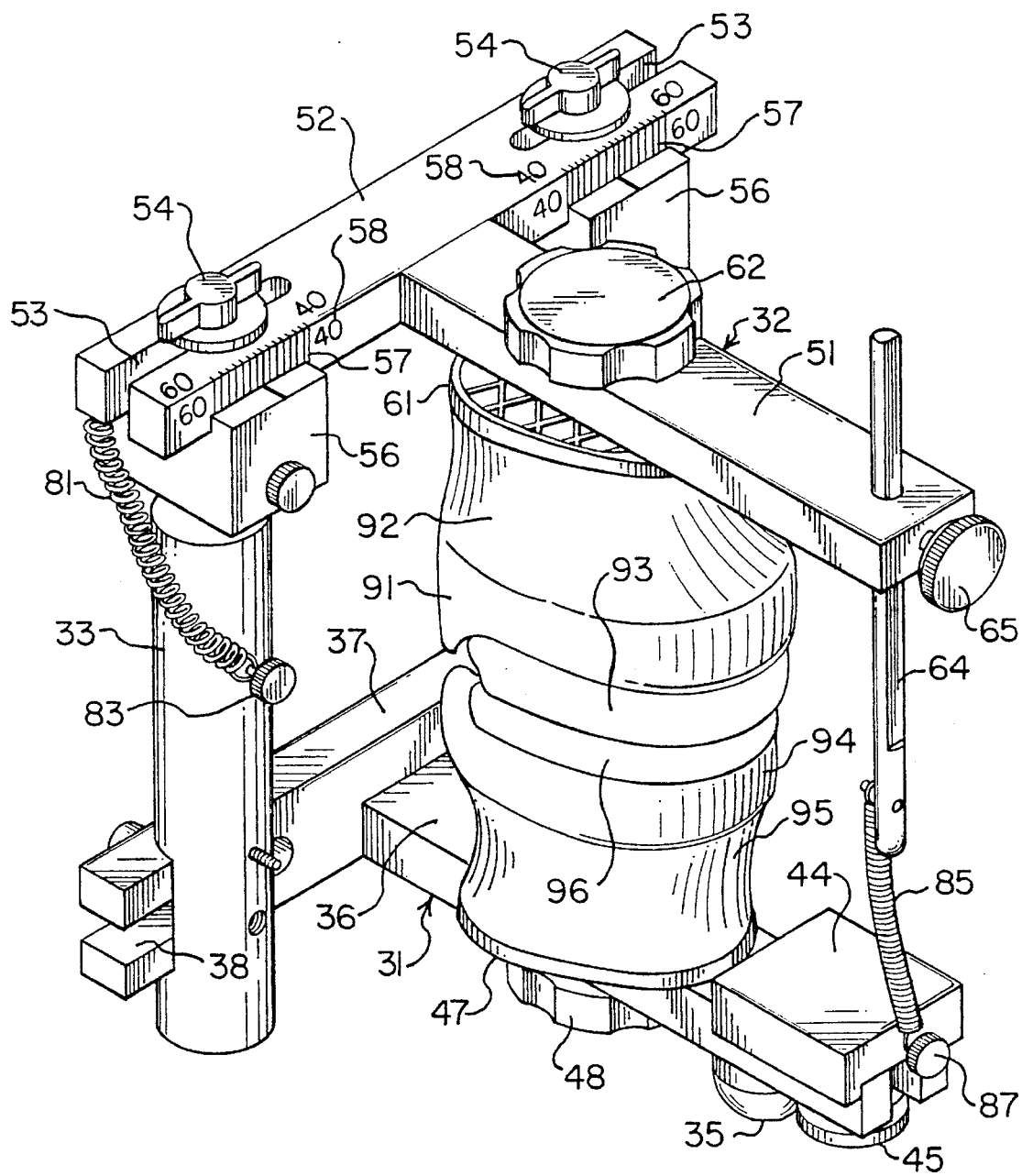
FIG. 12 is a perspective view of the articulator shown in FIG. 11.
Figure 13:
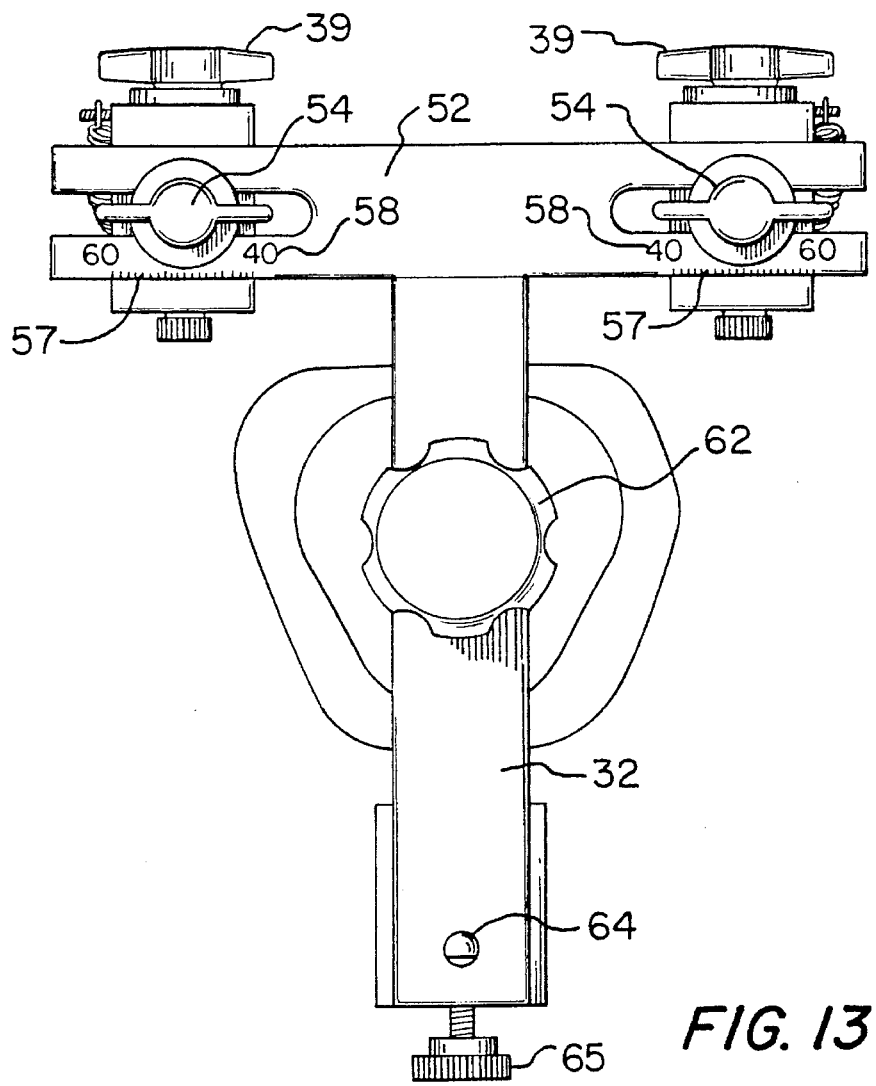
FIG. 13 is a top plan view of the articulator shown in FIGS. 11 and 12.
Figure 14:
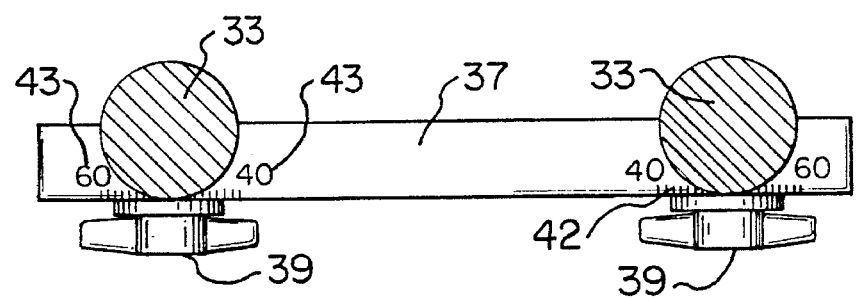
FIG. 14 is a sectional view taken along lines 14—14 of FIG. 11.
Figure 15:
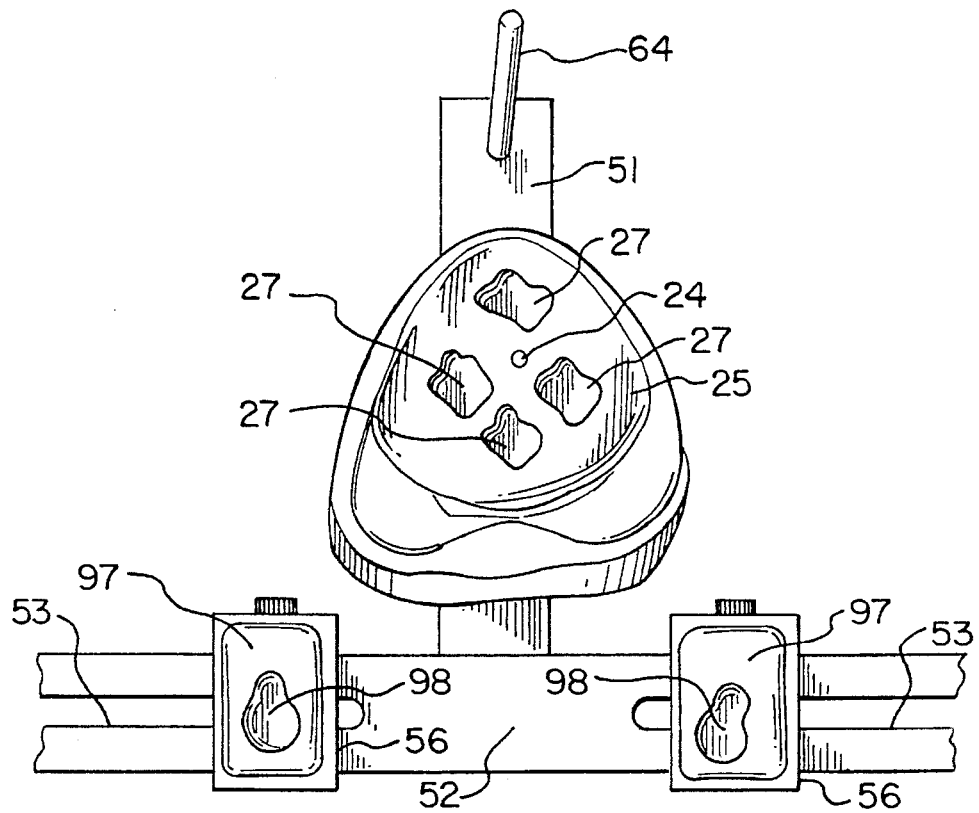
FIG. 15 is a plan view of the upper frame of the articulator in an inverted position showing the mandibular joint socket patterns in the side fossa holders.
Figure 16:
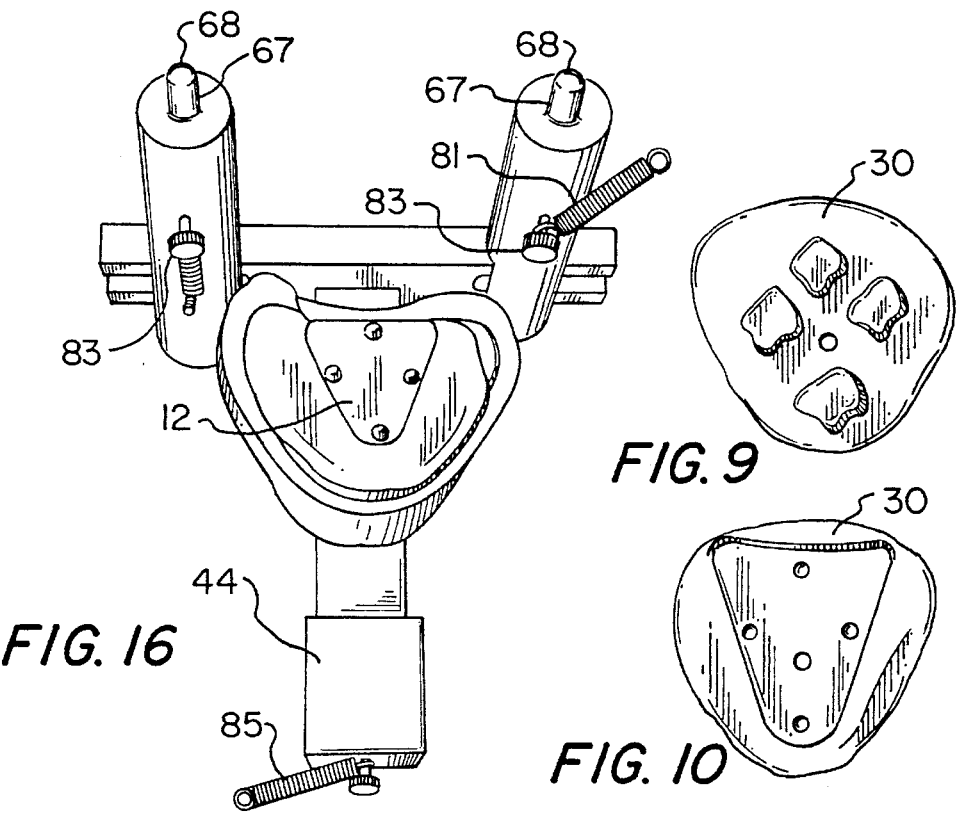
FIG. 16 is a top plan view of the lower frame of the articulator shown in FIGS. 11–14 with the upper frame removed.

An upper marking plate 17 generally corresponds in size and shape to the lower marking plate and has a rear depression or dimple 18, front depression or dimple 19, left side depression or dimple 20 and right side depression or dimple 21 disposed in an array directly opposite of the four marking pins of the lower marking plate and initially is formed with a bore or hole 22 that is generally centered in relation to the arrangement of the four depressions on the upper marking plate. More particularly the hole 22 is a relative short selected distance forwardly of the side depressions 20 and 21. This locates the bearing pin 24 described hereinafter and shown in FIG. 7 in front of the patterns 27 and is the third point of a tripod with the patient's mandibular joints facing the other two points of the tripod. The depressions are rounded and complementary in shape with the rounded surface portions of the marking pins to receive and mate with the rounded top surface portions. The lower marking plate and associated marking pins and the upper marking plate preferably are made of a hard, rigid, molded, plastic material.

Both lower and upper base plates with connecting bodies and upper and lower marking plates are placed in the patient's mouth and the upper marking plate 17 is placed on the lower marking pins 13–16 (the depressions in the upper marking plate are made to align with the lower marking pin) so that the metal bearing pin 24 and the upper marking plate 17 will not interfere with the marks or patterns 27 made by the lower marking pins. The patient then closes their mouth and the upper marking plate 17 is then transferred to the upper base plate 9 in the correct position. The upper marking plate 17 and body 3 are chilled in water to harden the positioning and fastening plastic body 3 which serves to fasten plate 17 to base plate 9. While the upper marking plate 17 is out of the patient's mouth a metal bearing pin 24 having external threads 24a in one end portion is threaded into the hole 22 in the upper marking plate 17 and checked against the lower marking plate 12 to have about an eight of an inch clearance between the upper and lower marking plates.

A soft moldable plastic such as friendly plastic is made into a wafer 25 about the diameter of a quarter and about a quarter inch thick. This wafer material is placed over the projecting portion of the metal bearing pin 24 and smoothed out to cover the upper marking plate 17 and the metal bearing pin 24. Then both the upper and lower marking plates with base plates are placed back in the mouth of the patient and the patient closes the mouth until the metal bearing pin 24 is riding against the top face of the lower marking plate 12. The patient then moves the mandible in all directions, back and forth and side to side. This forms four spaced three-dimensional identical tracks or socket patterns 27 in the wafer 25 which represents the movements of the mandible. In practice, the four patterns or tracks 27 formed in the wafer are spaced apart such that they do not interfere with each other and do not interfere with the marking pins. Each track or pattern 27 is a three-dimensional path similar to a shallow bowl. The upper marking plate 17 with wafer 25 is removed and chilled and forms into a hard, rigid body.

Figure 9:
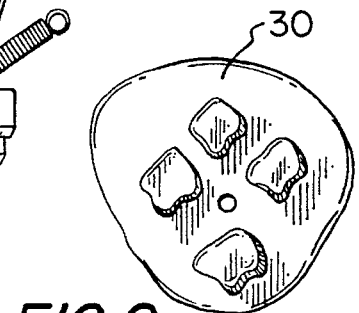
FIG. 9 is a top plan view of a registration body used to align the lower study model with the upper study model on the articulator.
Figure 10:
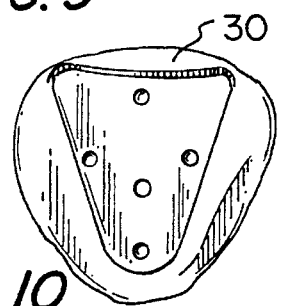
FIG. 10 is a bottom plan view of the registration body shown in FIG. 9.

The upper assembly including upper base plate 9, upper marking plate 17 and then put back in the mouth and a silicone impression material is injected around the lower marking pins while the patient holds the mandible back in a retruded position and there is pressure against the metal bearing pin 24. The silicone injection hardens to form a registration body 30 and is then removed. This registration body 30 is shown in FIGS. 9 and 10.

Referring now to FIGS. 11–14 the articulator shown has a lower frame 31 and an upper frame 32 with a pair of laterally spaced upright side posts 33 attached to the sides of the lower frame and supporting the upper frame 32 on the lower frame 31. The lower frame 31 is generally T-shaped having a central base member 36 to which is connected a rear cross member 37. A slot 38 is provided in both ends of the cross member 37 and a thumb screw 39 extends through the slot and threads into internal threads in a hole in the side post 33 to allow the side members to be moved to selected spacing distances relative to the lower frame. A front leg 35 is mounted under the base member. Equally spaced distance scale lines 42 with distance indicia 43 (shown as numerals 60 and 40) are provided on the cross member to indicate the spacing or width of the side posts 33. A block 44 fits on the forward end of the central base member 36 and is removably held in place by a thumb screw 45 underneath member 36 and extending up through and threading into block 44. A lower study model holder 47 fits on a central part of the central base member 36 and is releasably held by a thumb screw 48 underneath and threading into the holder 47.

The upper frame 32 is also generally T-shaped having an upper central base member 51 to which is connected an upper rear cross member 52. A slot 53 is provided in both ends of the cross member 52 and a thumb screw 54 extends through each slot and threads into a hollow box-shaped side fossa holder 56 to allow the two laterally spaced side fossa holders to be moved to selected spacing distances relative to the upper frame 32. Equally spaced distance scale lines 57 with distance indicia 58 are provided on the upper rear cross member 52 to indicate the spacing between or width of side fossa holders 56. An upper study model holder 61 fits under a central part of the upper central base member 51 and is held by a thumb screw 62 on top of the cross member to removably fasten the upper holder 61 to the upper frame 32.

A front support pin 64 extends down through a hole in a front end portion of the upper central base member 51 and terminates above and in spaced relation to the lower frame. A thumb screw 65 holds the support pin 64 at selected vertical positions relative to the upper frame.

Each side post has a reduced diameter top pin portion 67 with a semi-spherical top surface 68 on the side support members and are received inside the side fossa holders 56.

A side coil spring 81 connects at one end to a pin 82 on the outside of each side fossa holder 56 to the front of a side post 33 by a thumb screw 83. A front coil spring 85 connects at its upper end to the lower end of the front support pin 64 at a pin 86 and at its lower end to block 44 by set screw 87. These three springs arranged in a tripod or triangular configuration are used to hold a constant tension on the upper and lower marking plates during formation of the fossa sockets as described hereafter.

The mounting of the above described lower base plate 8 and upper base plate 9 onto the articulator will now be described. A mounting fork with the registration body 30 is placed between the lower and upper base plates 8 and 9 in the mouth. A face bow is attached and adjusted. The measurement of the patient's intercondylar width is taken from the face bow reading. This reading is then transferred to the articulator by setting the width adjustments of the side posts 33 relative to member 37 and the fossa holders 56 relative to cross member 52. After the silicone forming the registration body 30 is set the face bow is removed and the patient is dismissed.

The face bow is taken to the lab and the lower and upper base plates 8 and 9 are mounted on the articulator. The upper base plate 9 is placed on the upper jaw plaster secondary study model 91 and with the face bow is correctly mounted on the articulator in the exact position as in the mouth and secured to holder 61 by plaster 92 in a conventional manner.

After the upper jaw study model 91 is mounted the registration body 30 is placed between the upper and lower study models and the lower jaw study model 94 is then mounted in the correct position by applying plaster 95 to lower study model holder 47.

Finally the fossa sockets are made in the fossa holders by placing a soft acrylic material 97 in the articulator fossa holders and the upper articulator member is used to follow the tracks in the wafer 25 to form fossa socket patterns 27. The material 97 hardens when exposed to the air for a short time to form rigid socket patterns. The assembly shown in FIGS. 11–16 is now ready so that the teeth can be set to the exact patient's bite or centric relation. The upper marking plate 17 and the lower marking plate 12 and the wafer 25 are removed from the assembly shown in FIGS. 11–16. A plaster index of the upper and lower base plates is made. The upper neutral zone 93 and the lower neutral zone 96 are removed from the associated base plates and artificial teeth are set in the upper and lower base plates in a conventional manner. The lower frame will move according to the fossa socket patterns 98 in the fossa socket holders 99 and the teeth may be set with the correct occlusion.

Although the present invention has been described with a certain degree of particularity, it is understood that the present disclosure has been made by way of example and that changes in details of structure may be made without departing from the spirit thereof.

What is claimed is:

1. In a dental articulator for substantially duplicating a temporomandibular joint of a patient, the combination comprising:

a lower frame with a pair of upstanding laterally spaced side posts, each said side post having a pin-like upper section with a top portion of generally semi-spherical shape, a lower jaw model of a particular patient supported by said lower frame, a lower base plate supported by said lower jaw model, a lower marking plate mounted to said lower base plate and having four upstanding, spaced marking pins, said pins being spaced apart a sufficient distance from one another in relation to patient jaw movement to avoid a socket pattern overlap, an upper frame supporting a pair of laterally spaced fossa holders receiving said upper sections with a pliable mold material disposed in each of said fossa holders, an upper jaw model of a particular patent supported by said upper frame, an upper marking plate mounted to said upper jaw model opposite said lower marking plate and having a wafer attached to a bottom face, said wafer having four spaced socket patterns in which top portions of said marking pins are disposed, said four socket patterns being representative of the movement of the lower jaw of a particular patient, tension means extending between said lower and upper frames whereby the movement of one of said upper and lower frames relative to one another with said marking pins track in said four socket patterns form a fossa socket pattern in said mold material in each of said holders that are a substantial duplication of the temporomandibular joints of a patient, said mold material hardening after said fossa socket patterns are formed.

2. In a dental articulator as set forth in claim 1 wherein said side posts are adjustably movable relative to said lower frame to accommodate different jaw widths with distance scale lines and distance indicia on said lower frame and side posts to indicate the spacing of said posts.

3. In a dental articulator as set forth in claim 1 wherein said fossa holders are adjustably movable relative to said upper frame to accommodate different jaw widths with distance scale lines and distance indicia on said upper frame and fossa holders to indicate spacing of said fossa holders.

4. In a dental articulator as set forth in claim 1 wherein said fossa holders are a hollow, generally rectangular body open along the bottom.

5. In a dental articulator as set forth in claim 1 including a support pin extending down from said upper frame and wherein said tension means includes a side coil spring connected between a rear portion and along the outside of one of said fossa holders and a front of one of said side posts intermediate the ends of said side post and a front coil spring extending down from a lower end portion of said support pin to a block at the front end of said lower frame to provide triangular-shaped applications of forces to hold said upper and lower marking plates together.

6. In a dental articulator as set forth in claim 5 wherein said support pin is adjustably movable relative to said upper frame.

7. In a method of making a recording of the temporomandibular joints of a patient comprising:

taking impressions of upper and lower jaws in a mouth of a patient, making upper and lower base plates corresponding to the shape of the inside of the patient's mouth, making a lower marking plate having four upstanding spaced marking pins, said marking pins being a front marking pin and a rear marking pin positioned along a longitudinal center line a selected distance from one another and left side and right side a selected distance to the side of said longitudinal center line, said pins being spaced apart a sufficient distance from one another in relation to patient jaw movement to prevent a socket pattern overlap, making an upper marking plate having four depressions that line up and mate with end portions of said marking pins, attaching said upper marking plate to said upper base plate and said lower marking plate to said lower base plate, placing the upper marking plate on the lower marking plate with its depressions aligning with the pins, placing said base plates and said marking plates in the mouth of a patient, having the patient bite together so that the four pins go into the four depressions and the upper marking plate is transferred to the upper base plate in the exact position, taking the upper and lower marking plates out of the mouth of the patient, attaching a bearing pin to said upper marking plate, placing a wafer of soft pliable material around said bearing pin between said upper and lower marking plates, putting the upper and lower base plates back in the mouth of the patient, having the patient close the mouth until said bearing pin touches the top surface of the lower base plate, having the patient move the lower jaw back and forth, front to rear and side to side and the four pins make four socket patterns in the wafer representative of the movement of the lower jaw of the patient, having the patient bite down and retract to form a registration body, and placing the upper and lower study models of a particular patient on an articulator with said registration body aligning said lower jaw model with said upper jaw model to duplicate extent of jaw movement.

\* \* \* \* \*